(12) United States Patent
Barth et al.

(10) Patent No.: US 6,706,203 B2
(45) Date of Patent: Mar. 16, 2004

(54) ADJUSTABLE NANOPORE, NANOTOME, AND NANOTWEEZER

(75) Inventors: Philip W. Barth, Portola Valley, CA (US); Daniel B. Roitman, Menlo Park, CA (US); Joel Myerson, Berkeley, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 278 days.

(21) Appl. No.: 10/022,452

(22) Filed: Oct. 30, 2001

(65) Prior Publication Data

US 2003/0080042 A1 May 1, 2003

(51) Int. Cl.[7] .............................. H01L 21/00; B44C 1/22
(52) U.S. Cl. ............................. 216/33; 216/56; 438/733
(58) Field of Search .............................. 216/33, 56, 83, 216/99; 438/719, 733, 745, 752, 753, 756; 935/85, 99

(56) References Cited

U.S. PATENT DOCUMENTS

| | | | |
|---|---|---|---|
| 4,343,993 | A | 8/1982 | Binnig et al. |
| 5,699,462 | A | 12/1997 | Fouquet et al. |
| 5,795,782 | A | 8/1998 | Church et al. |
| 5,842,387 | A | 12/1998 | Marcus et al. |
| 5,954,079 | A | 9/1999 | Barth et al. |
| 5,960,131 | A | 9/1999 | Fouquet et al. |
| 6,055,344 | A | 4/2000 | Fouquet et al. |

OTHER PUBLICATIONS

MinFeng Yu et al, "Three–dimensional manipulation of carbon nanotubes under a scanning electron microscope", Nanotechnology, vol. 10, No. 3, pp. 244–252 (Sep. 1999).

J. Appenzeller et al, "Scheme for the fabrication of ultrashort channel metal–oxide–semiconductor field–effect transistors", Applied Physics Letters. vol. 77. No. 2, pp. 298–300 (July 10, 2000).

S. K. Ghandhi, "VLSI Fabrication Principles: Silicon and Gallium Arsenide", John Wiley & Sons, New York, pp. 8–10 (1983) ISBN 0–471–86833–71.

C. Cowache et al, "Evaluation of advanced pre–gate cleanings", Cleaning Technology in Semiconductor Device Manufacturing. Proceedings of the Sixth International Symposium, Electrochemical Society Proceedings, vol. 99–36, pp. 59–68 (2000).

J.N. Israelachvili, "Intermolecular and Surface Forces", Section 10.7. pp. 14–15, 54–57, and 168–175, Academic Press New York, (1995).

S.K. Ghandi, "VLSI Fabrication Principles: Silicon and Gallium Arsenide", Wiley–Interscience, p. 5 (1983) ISBN 0 471–86833–7.

(List continued on next page.)

Primary Examiner—William A. Powell

(57) ABSTRACT

An adjustable nanopore is fabricated by placing the surfaces of two planar substrates in contact, wherein each substrate contains a hole having sharp corners and edges. A corner is brought into proximity with an edge to define a triangular aperture of variable area. Ionic current in a liquid solution and through the aperture is monitored as the area of the aperture is adjusted by moving one planar substrate with respect to the other along two directional axes and a rotational axis. Piezoelectric positioners can provide subnanometer repeatability in the adjustment process. The invention is useful for characterizing, cleaving, and capturing molecules, molecular complexes, and supramolecular complexes which pass through the nanopore, and provides an improvement over previous devices in which the hole size of nanopores fabricated by etching and/or redeposition is fixed after fabrication.

63 Claims, 9 Drawing Sheets

OTHER PUBLICATIONS

V. Milanovic et al, "Deep Reactive Ion Etching for Lateral Field Emission Devices", IEEE Electron Device Letters, vol. 21, No. 6, pp. 271–273 (Jun. 2000).

R.B. Marcus et al, "The Oxidation of Shaped Silicon Surfaces", The Journal of the Electro–Chemical Society, vol. 129, No. 6, pp. 1278–1282 (1982).

R.B. Marcus et al, "Formation of silicon tips with <1 num radius", Applied Physics Letters, vol. 56, No. 3, pp. 236–238 (Jan. 15, 1990).

T.S. Ravi et al, "Oxidation sharpening of silicon tips", Journal of Vacuum Science and Technology, vol. B9, No. 6, pp. 2733–2737 (Nov./Dec. 1991).

W.R. Ashurst et al, "Dichlorodimethylsilane as an Anti–Stiction Monolayer for MEMS", Journal of Microelectromechanical Systems, vol. 10, No. 1, pp. 41–49 (Mar. 2001).

Bruce Alberts et al, "The Molecular Biology of the Cell", 3rd ed., Garland Publishing, New York, pp. 408–413 (1994) ISBN 0–8153–1619–4.

W. Vercoutere et al, "Rapid discrimination among individual DNA hairpin molecules at single–nucleotide resolution using an ion channel", Nature Biotechnology, vol. 19, No. 3 pp. 248–252 (Mar. 2001).

T.R. Albrecht et al, "Microgabrication of integrated scanning tunneling microscope", Journal of Vacuum Science Technology, vol. A8, No. 1, pp. 317–319 (Jan./Feb. 1990).

B. Alberts et al, "Molecular Biology of the Cell", Garland Publishing, 3rd ed., pp. 89–138 (1994).

D.N. Petsev et al, "Evidence for Non–DLVO Hydration Interactions in Solutions of the Protein Apoferritin", Physical Review Letters, vol. 84, No. 6, (Feb. 7, 2000).

K. Vepa et al, "A Method for Native Oxide Thickness Measurement", Electrochemical Society Proceedings, vol. 95–20, pp. 358–365.

J. Li et al, "Ion Beam Sculpting at Nanometre Length Scales", Nature, vol. 412, pp. 166–169 (Jul. 12, 2001).

Tersoff, "Less is More", Nature, vol. 412, pp. 135–136 (Jul. 12, 2001).

ADJUSTABLE NANOPORE, NANOTOME, AND NANOTWEEZER

TECHNICAL FIELD

The present invention relates generally to handling, measurement, and cleavage of objects at the molecular size scale, that is, with handling, measurement, and cleavage of objects with characteristic dimensions on the order of nanometers.

BACKGROUND ART

The art of manipulating individual atoms, molecules, and supramolecular particles is called "nanomanipulation", and is in a very crude state in the year 2001.

The art of nanomanipulation was first proposed by Richard Feynman on Dec. 29, 1959, at the annual meeting of the American Physical Society in a speech titled "There's Plenty of Room at the Bottom", in which he noted that "The principles of physics, as far as I can see, do not speak against the possibility of maneuvering things atom by atom. It is not an attempt to violate any laws; it is something, in principle, that can be done; but in practice, it has not been done because we are too big."

Feynman, the winner of the 1965 Nobel Prize in physics, further noted in his 1959 speech that "The problems of chemistry and biology can be greatly helped if our ability to see what we are doing, and to do things on an atomic level, is ultimately developed—a development which I think cannot be avoided."

However, progress in nanomanipulation has been slow.

The scanning tunneling microscope (STM) was developed in 1980; see U.S. Pat. No. 4,343,993. The STM provides, in essence, a means of shoving around atoms and molecules on a slab with a pointy stick. It also provides a crude sense of touch. The atomic force microscope (AFM) was developed subsequently and provides another means of shoving atoms and molecules on a slab with a pointy stick, and also provides a crude sense of feel. Other proximal probe microscopy (PPM) techniques were developed subsequently; all consist of a pointy stick whose tip position is controlled and monitored, and which can report on the profile and properties of a surface over which the stick is dragged. The usual means of controlling the stick's tip position is a three-axis piezoelectric driver, and the usual means of sensing the tip position is a combination of sensing the voltages applied to the piezoelectric driver and sensing some other quantity such as tunneling current, piezoresistive change, or optical reflection occurring as close as possible to the tip. Scanning probe techniques have been combined with electron microscopy to provide additional sensing means; see, for example "Three-dimensional manipulation of carbon nanotubes under a scanning electron microscope", by MinFeng Yu et al, *Nanotechnology*, Vol. 10, no. 3, pp. 244–252 (September 1999).

More recently, naturally occurring pores in cell membranes have been used to characterize long-chain molecules; see, for example, U.S. Pat. No. 5,795,782. These pores have fixed dimensions on the order of nanometers. Subsequently, artificially-produced nanopores of fixed dimensions have been developed for the same purpose. Both types of pores have been used to sense the passage of individual long-chain molecules such as DNA molecules, and have provided some information on the structure of such molecules. The "holy grail" of these techniques, not yet achieved, has been to sense the structure of a molecule passing through a pore to a level as fine as the individual bases in a DNA strand.

The usual means of sensing the passage of a molecule through the pore is to monitor ionic current through a solution filling the pore when a voltage is applied. Reduction in a maximum current implies that the pore is partly blocked by the cross-sectional area of a molecule. Charged molecules float freely in solution, and at random times are pulled through the pore by an electric field existing in the solution. One problem with these techniques is that the passage of an individual molecule through a pore cannot be precisely predicted or controlled; it is a random, stochastic event, and when a molecule enters the pore, it zips through quickly.

Thus, there still exists a need for other means of manipulating and sensing atoms and molecules, and other entities larger than molecules.

DISCLOSURE OF INVENTION

The present invention forms an adjustable nanopore, nanotome, or nanotweezer by placing two substrates in close contact such that they form a small adjustable aperture through which a continuous path extends. A first substrate has a first edge situated at a first surface of the first substrate, the first edge having a first region of sharp curvature in the plane of the first surface. A second substrate has a second edge situated at a second surface of the second substrate. The first surface is placed in close contact with the second substrate such that the first edge and the second edge combine to form an arched aperture, the first edge forming the arch, the first region of sharp curvature forming the crown of the arch, the second edge forming the base of the arch, and the two closest approach points of the first and second edges forming the springing points of the arch. The second edge may be straight, or may be curved either convexly toward or concavely away from the first edge. The second edge can be moved with respect to the first edge, using an adjustable movement mechanism, to vary the height of the arch, the area of the arch, and the shape of the arch. The width of the aperture is defined as the diameter of the largest sphere which can pass through the aperture, and this width can be one hundred nanometers and less. The arched aperture can be usefully employed in characterizing, sorting, sieving, cleaving, and holding nanometer-scale substances including molecules, molecular complexes, and supramolecular complexes, and mixtures thereof.

In accordance with several embodiments of the present invention, two monolithic substrates are provided, each having a through-hole, with the first through-hole in the first substrate intersecting a first surface at a first edge, the first edge having a corner region of sharp curvature in the plane of the first surface with a radius of curvature on the order of 3 nanometers, the first through-hole and the first edge being preferably formed by orientation-dependent etching. The second through-hole in the second substrate intersects a second surface at a second edge, and the second hole and second edge are also preferably formed by orientation dependent etching. The first surface is placed in contact with the second surface such that the first edge and second edge combine to form an arched aperture of substantially triangular cross section, the corner region in the first edge forming the crown of the arch or the apex of the triangle. A mechanism is provided to move one substrate relative to the other so as to adjust the size and shape of the aperture.

In one embodiment (nanopore), the first edge and the second edge combine to create a pore of adjustable area and substantially triangular cross section through which a molecule can pass, so as to provide information about the molecule or to separate molecules of different dimensions, such as separating straight-chain hydrocarbons from branched hydrocarbons.

In a second embodiment (nanotome), the first edge and the second edge combine to create a pore of adjustable area and substantially triangular cross section around a stretched long-chain molecule. The area of the pore is then reduced to create a shearing action so as to cut the molecule at a desired point.

In a third embodiment (nanotweezer), the first edge and the second edge combine to create a pore of adjustable area and substantially triangular cross section around a stretched long-chain molecule. The area of the pore is then reduced to capture the molecule at a desired point without cutting it.

In the three embodiments discussed above, the arched aperture is substantially triangular (symmetrical or asymmetrical), and the height of the triangle is altered by moving one element relative to the other, e.g., moving the second edge (base) closer to or further away from the corner (crown or apex) in the first edge.

Alternatively, a second corner region of sharp curvature in the second edge may be formed, and the corner region in the first edge may be combined with the corner region in the second edge to form an arched aperture which is substantially square, more generally substantially rectangular, or more generally substantially rhomboid, in which the area of the rhombus is altered by moving one corner relative to the other corner.

The above embodiments rely on the combined use of corners and edges which can be built with atomically precise dimensions, or with dimensions which are nearly atomically precise, and which can be juxtaposed with long-chain molecular preparations to manipulate such preparations and to provide information on the properties of such preparations.

More generally, the present invention relies on the combined use of a first substrate having a first surface intersected by a first edge having a region of sharp curvature in the plane of the first surface, and a second substrate having a second surface intersected by a second edge, the two edges being juxtaposed with molecular preparations to manipulate such preparations and to provide information on the properties of such preparations. The molecular preparations can include molecules, molecular complexes, ands supramolecular complexes.

In one embodiment, the nanopore of the present invention comprises two monolithic substrates, each containing a through-hole created by orientation-dependent etching. The two substrates are placed in contact with one another in such a manner that the through-holes are placed adjacent to one another, so that a continuous passage through both substrates exists. Further, the two substrates are rotationally adjusted with respect to one another using a goniometer so that a sharp corner of one through-hole is adjacent a sharp edge of the other through-hole, thus creating a nanopore of triangular cross-section. The cross-sectional area of the triangular nanopore is adjusted by moving the corner with respect to the edge using one or more piezoelectric positioners. The shape of the triangular nanopore is adjusted by rotating the corner with respect to the edge using a goniometer.

Specifically, in accordance with a further aspect of the present invention, a method for fabricating the nanopore is provided, which comprises:
providing a first substrate having a flat first major surface;
forming a first edge lying in the plane of the first major surface, the edge having a first region of sharp curvature in the plane of first surface;
providing a second substrate having a flat major second surface;
forming a second edge laying in the plane of the second surface,
placing the first surface in contact with the second surface in such a fashion that the second edge and the first region of sharp curvature form an aperture; and
providing adjustment means to control the width of the aperture.

An ionic solution filling the nanopore has an electrical conductance through the pore which is proportional to the cross-sectional area of the pore. As the cross-sectional area of the pore is adjustably reduced and approaches zero, the ionic conductance through the pore is reduced and approaches zero, and the curve of conductance versus position changes slope when the pore cross-sectional area is reduced to zero. The change in slope, rather than a complete reduction to zero current, occurs because leakage current occurs along the interface between the two substrates, which interface has some roughness allowing some penetration of the ionic solution.

Long-chain polymer molecules which pass through the adjustable nanopore when no adjustment of pore area is being performed interfere with the flow of ionic current, and so the ionic current at constant cross-sectional area may be measured to monitor the passage of such long-chain polymers or to otherwise characterize and/or handle such molecules.

Thus, in accordance with another aspect of the present invention, a method of at least one of characterizing and handling at least one substance selected from the group consisting of molecules, molecular complexes, and supramolecular complexes and mixtures thereof is provided, comprising:
providing a nanopore having a width, the nanopore including a mechanism for adjusting the width of the nanopore;
placing the nanopore in an ionic solution containing at least one copy of the substance to be characterized so that a continuous path of the ionic solution through the nanopore is established;
adjusting the width of the nanopore to a desired first width;
establishing an ionic electric current of desired direction and magnitude through the nanopore; and
sensing at least one of the entrance into the nanopore of the substance to be characterized and the blockage by the nanopore of the path of the substance to be characterized, the sensing occurring by means of a change in the magnitude of the ionic current.

If it is desired to cleave a long molecule, the area of the adjustable nanopore may be changed while electrical current monitoring indicates that the molecule is passing through the nanopore. In this event, the apparatus of the present invention exerts a scissoring action in the molecule, acting to cleave it into two molecules, and the apparatus may be considered to act as a "nanotome", by analogy with the prior-art microtome which cuts thin sheets of material off of a larger sample.

Thus, in accordance with yet another aspect of the present invention, a method of cleaving at least one substance selected from the group consisting of molecules, molecular complexes, and supramolecular complexes and mixtures thereof is provided, comprising:
providing the nanopore;
placing the nanopore in an ionic solution containing at least one copy of the substance to be cleaved so that a continuous path of the ionic solution through the nanopore is established;

adjusting the width of the nanopore to a desired first width;

establishing an ionic electric current of desired direction and magnitude through the nanopore;

sensing the presence in the nanopore of the substance to be cleaved, the sensing occurring by means of a change in the magnitude of the ionic current; and decreasing the width of the nanopore to a second width small enough to cleave the substance.

If it is desired to capture a long molecule for purposes of manipulation, the area of the adjustable nanopore may be changed while electrical current monitoring indicates that the molecule is passing through the nanopore. In this event, the apparatus of the present invention captures the molecule, and the apparatus may be considered to act as a "nanotweezer", by analogy with a simple tweezer in which two prongs capture a small part. In contrast to a simple tweezer which, as it captures a part, suddenly localizes it in three dimensions, the nanotweezer serves to first localize the molecule in two dimensions before capturing it to localize it in a third dimension.

Thus, in accordance with a still further aspect of the present invention, a method of capturing at least one substance selected from the group consisting of molecules, molecular complexes, and supramolecular complexes and mixtures thereof is provided, comprising:

providing the nanopore;

placing the nanopore in an ionic solution containing at least one copy of the substance to be captured so that a continuous path of the ionic solution through the nanopore is established;

adjusting the width of the nanopore to a desired first width;

establishing an ionic electric current of desired direction and magnitude through the nanopore;

sensing the presence in the nanopore of the substance to be captured, the sensing occurring by means of a change in the magnitude of the ionic current; and decreasing the width of the nanopore to a second width small enough to capture the substance and hold it.

BRIEF DESCRIPTION OF THE DRAWINGS

FIG. 1b is a plan view of the embodiment depicted in FIG. 1a, wherein the cross-section of FIG. 1a is taken along the line 1a–1a;

FIG. 2a depicts the bottom surface of the chip and FIG. 2b depicts the top surface of the chip;

FIG. 5b is a cross-sectional view, taken along the lines 5b–5b of FIG. 5a,

FIG. 6b is a cross-sectional view, taken along the lines 6b–6b of FIG. 6a;

FIG. 7b is a cross-sectional view, taken along the lines 7b–7b of FIG. 7a.

BEST MODES FOR CARRYING OUT THE INVENTION

The description which follows is presented in terms of a specific single-crystal material, namely, silicon, for which etching along certain crystallographic directions provides through-holes having desired properties. However, there are other single crystal materials, including, but not limited to, germanium, quartz, and diamond, that may be employed in the practice of the present invention. Further, polycrystalline materials may also be utilized, including, but not limited to, silicon, germanium, quartz, and diamond, to the extent that such polycrystalline materials exhibit localized orientation-dependent etching characteristics enabling the fabrication of a local corner in one polycrystalline substrate which can be juxtaposed with a local edge on another substrate comprising the same or a different material. Further, amorphous materials, e.g., glasses or ceramics, may be used to the extent that a local edge can be fabricated in an amorphous substrate by techniques such as ion bombardment, fracturing and etching. The local edge can be juxtaposed with a sharp local corner fabricated in another substrate comprising the same or a different material. Further, amorphous materials may be used to the extent that a sharp corner can be fabricated in an amorphous substrate by techniques such as ion beam milling. The sharp corner can be juxtaposed with a sharp edge fabricated in another substrate comprising the same or a different material.

Figure 1A:
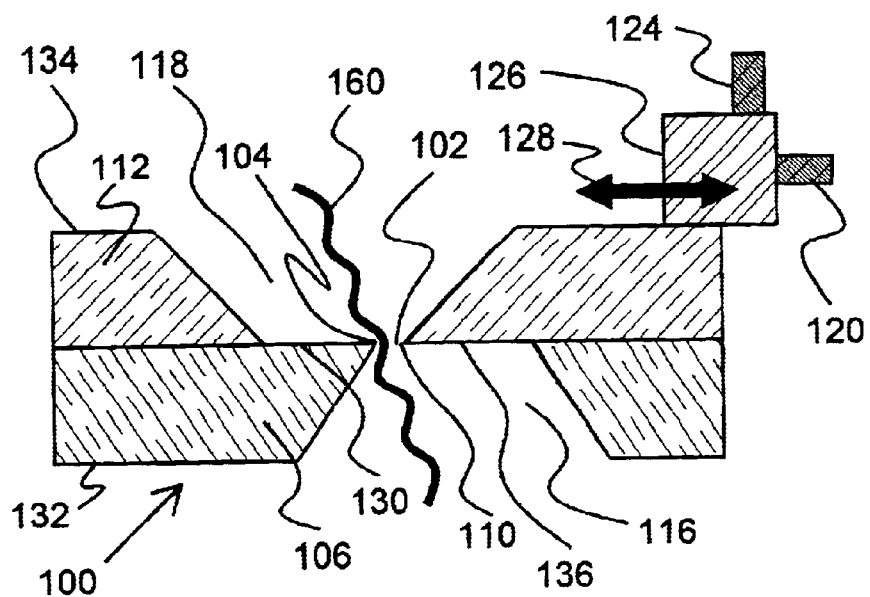
FIG. 1a is a cross-sectional view of a first embodiment of the present invention, depicting a nanopore comprising an upper silicon chip supported on a bottom silicon chip, with one chip movable relative to the other.
Figure 1B:
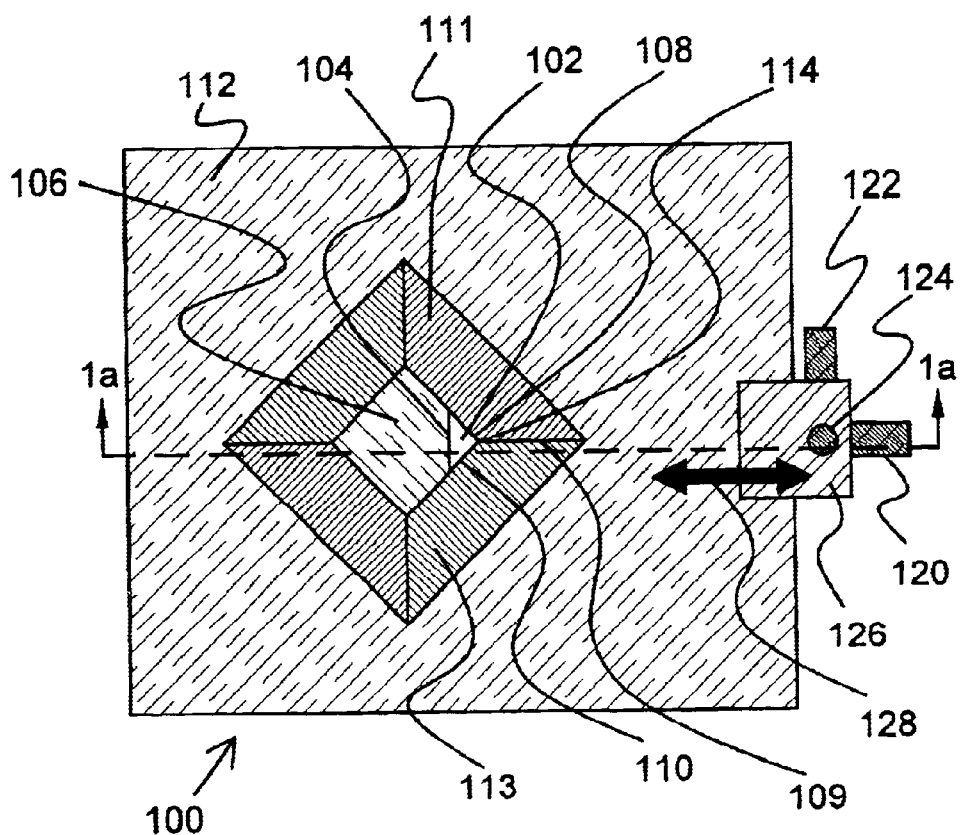

FIG. 1a illustrates a cross-sectional view of embodiment 100 of the invention and FIG. 1b illustrates a plan view of the same embodiment. Cross-section line 1a–1a in FIG. 1b indicates the cross-section shown in FIG. 1a. This first embodiment is called a nanopore, for reasons which will become evident.

A long molecule 160, shown in FIG. 1a but not shown in FIG. 1b, extends through pore 102 which is bounded by edge 104 in lower chip 106 and edges 108 and 110 in upper chip 112. Edge 104 viewed from the perspective of FIG. 1a has a convex angle of 35.3°. Edges 108 and 110, if viewed from directions (not shown) running along the directions of the edges, also have a convex angle of 35.2°. Corner 114 viewed from the perspective of FIG. 1b is formed by the meeting of edges 108 and 110, and has a concave angle of 90°. Groove 109 is formed by the intersection of planes 111 and 113, and if viewed from a direction (not shown) along groove 109 has a concave angle of 109°. Through-hole 116 is formed in lower chip 106 by orientation-dependent etching of silicon in a caustic solution such as tetramethyl ammonium hydroxide in water, and through-hole 118 in upper chip 112 is formed in a manner similar to hole 116. Orientation-dependent etching is discussed more fully below. Typical dimensions for a hole etched in a single crystal silicon chip are, for example, a square hole 100 μm (micrometers) on an edge at the narrowest area of the hole, the same hole being 842 μm on an edge at its widest area, and the overall dimensions of the silicon chip being 5 mm (millimeters) square and 525 μm thick.

A V-groove similar to groove 109 etched in silicon using KOH in water as the etchant has been shown by transmission electron microscopy (TEM) to have "a rounded shape that has a radius of curvature of around 3 nm" (J. Appenzeller et al, "Scheme for the fabrication of ultrashort channel metal-oxide-semiconductor field-effect transistors", *Applied Physics Letters*, Vol. 77, No. 2, pp. 298–300 (Jul. 10, 2000)). The sharpness of the groove tip in that work may have been limited because it was formed at a junction between heavily doped (n++) silicon and lightly doped (p−) silicon; thus it is reasonable to expect a radius of curvature of 3 nm or less in groove 109.

Actuators or positioners 120, 122, and 124 act on block 126, which is attached to upper chip 112. Actuators 120, 122, and 124 are preferably piezoelectric actuators similar to those used in STMs (scanning tunneling microscopes) and AFMs (atomic force microscopes), but other actuator types including, but not limited to, mechanical positioners, electromagnetic actuators, and electrostatic actuators may be used. Motion of upper chip 112 with respect to lower chip 106 is possible in all three spatial axes, but as long as the two chips are in contact or near contact, the motion is primarily actuated along the axis given by arrow 128, which acts to increase and decrease the cross-sectional area of pore 102. It is immaterial as to which chip the piezoelectric actuators act upon; it is merely required to move one chip relative to the other chip. Additional actuators (not shown) may be used to rotate chip 112 while it remains in contact or near contact with chip 106, or such rotation may be accomplished by other manual or automatic adjustment of a goniometer (not shown).

Chip 106 has upper surface 130 and lower surface 132. Chip 112 has upper surface 134 and lower surface 136. If the two surfaces 130 and 136 are in contact, then motion of chip 106 relative to chip 112 occurs in the presence of sliding contact between surfaces 130 and 136. However, sliding motion of chip 106 relative to chip 112 is not strictly necessary to the purposes of the present invention. Where stiction of the two surfaces 130 and 136 tends to impede sliding motion of chip 106 relative to chip 112, or for other reasons, the two surfaces 130 and 136 may be separated by a small distance using actuator 124 or another actuator or actuators (not shown) to allow relative translational or rotational motion, or both, to occur between chips 106 and 112. After relative motion of the separated chips is accomplished, surfaces 130 and 136 can again be placed in contact. Further, complete separation of surface 130 from surface 136 is not strictly necessary for the purpose of achieving motion in the presence of stiction. In order to achieve motion in the presence of stiction, or for other reasons, a slight tilt may be imposed on chip 112 with respect to chip 106, using either actuator 124 or another actuator or actuators (not shown), and leaving chip 112 in contact with chip 106 only along a line, or only at a point, or only at multiple points, thus greatly reducing stiction forces between surfaces 130 and 136 and more easily allowing relative motion to occur between chips 106 and 112 via sliding motion along the line contact or the point contact or the multiple point contacts. After relative motion is accomplished, the surfaces 130 and 136 can again be placed in contact.

One method of actuation which imposes a tilt is given, for example, in U.S. Pat. No. 5,954,079, "Asymmetrical Thermal Actuation in a Microactuator", and it is shown in that patent that tilting actuation offers improved control in the presence of physical phenomena which could lead to snap-off and snap-in. In that patent the physical phenomenon leading to snapping actuation was a thermal phenomenon. In the present invention, surface attraction and stiction due to Van der Waals forces and other forces can be expected to lead to snapping phenomena similar to those noted in, e.g., J. N. Israelachvili, *Intermolecular and Surface Forces,* Academic Press, New York, pp. 14–15 (1995), and section 10.7, and tilting actuation used to separate surfaces 130 and 136 is expected to reduce or eliminate such snapping phenomena. Various means of tilting actuation will occur to those skilled in the art and may be employed without departing from the scope and spirit of the present invention.

Figure 2A:
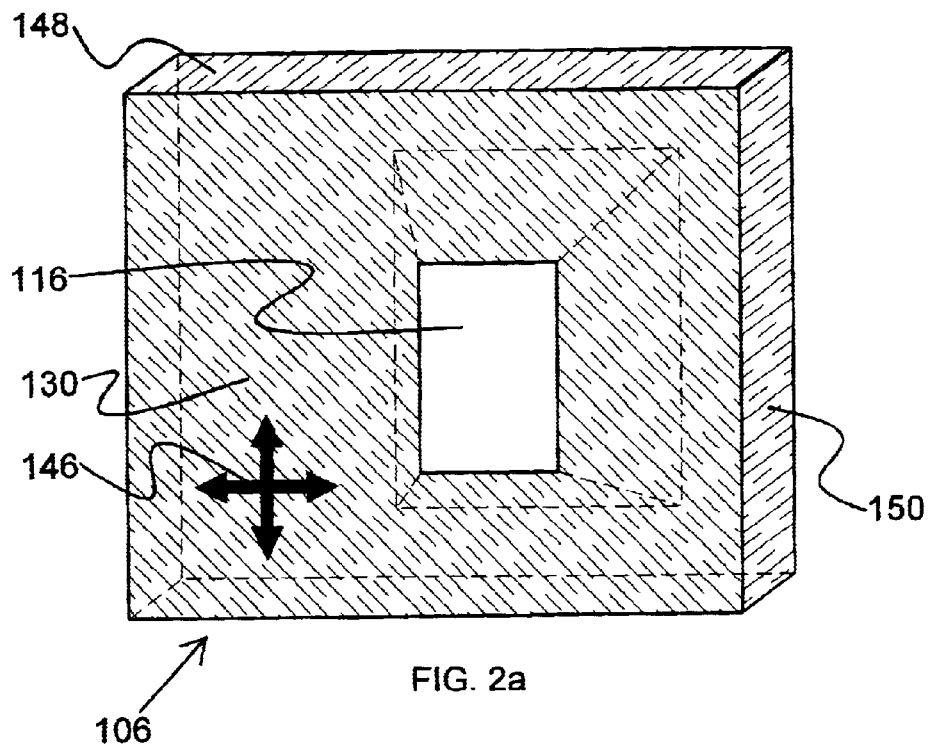
FIGS. 2a and 2b are isometric views of one of the silicon chips employed in the embodiment depicted in FIGS. 1a–1b, illustrating the orientation-dependent etching employed in the practice of the present invention, where
Figure 2B:
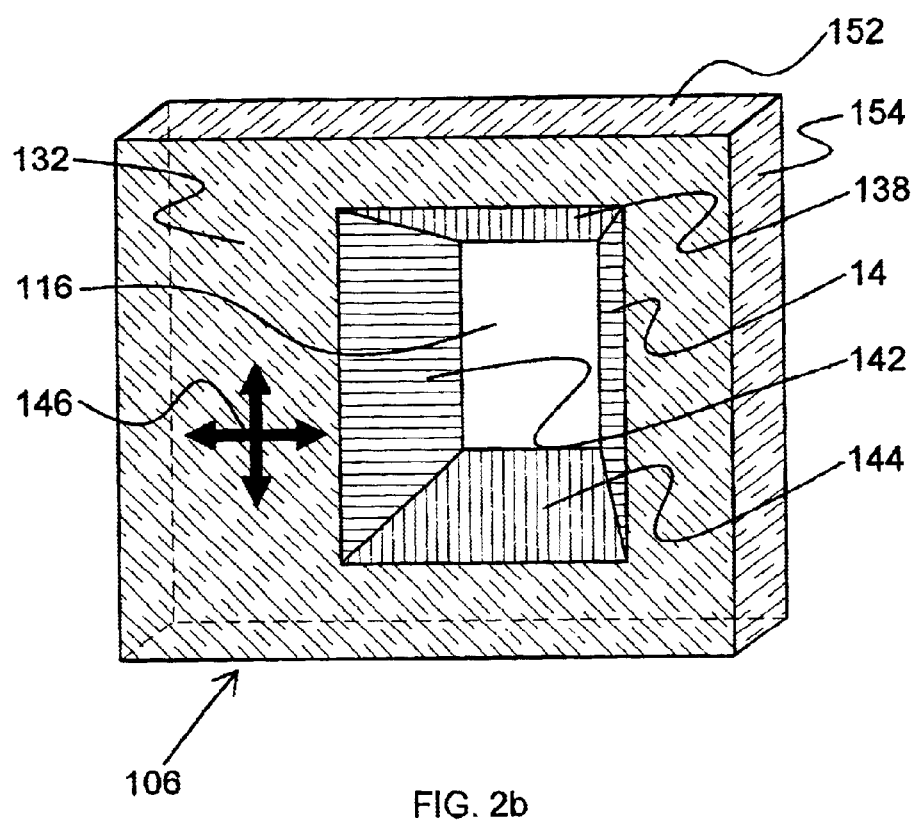

FIG. 2a shows an isometric view of chip 106 as seen from surface 130, and FIG. 2b shows an isometric view of chip 106 as seen from surface 132. Surfaces 130 and 132 are perpendicular to <100> crystalline directions in the [100]-oriented single-crystal silicon substrate from which chip 106 is formed. (For a discussion of crystal planes and directions see, for example, S. K. Ghandhi, VLSI Fabrication Principles, John Wiley & Sons, New York, pp. 8–10 (1983) ISBN 0-471-86833-7.) Through-hole 116 is bounded by etched planes 138, 140, 142 and 144, each of which is perpendicular to a <111> crystalline direction in the single crystal substrate. Axes 146 lie parallel to <110> directions in the single crystal substrate. Chip edges 148, 150, 152, and 154 are formed by sawing of chip 106 from a larger wafer of single crystal silicon, such sawing typically being performed after hole 116 is formed by etching, so that many holes such as 116 can be formed simultaneously before the silicon wafer is diced to form many chips such as chip 106.

Chip 112 is formed in the same manner as chip 106, and thus the details of the through-hole 118 are not depicted herein. The same considerations regarding etching of a [100]-oriented single crystal silicon substrate, and the planes formed thereby, obtain as in the etching of chip 106. Likewise, chip edges (not shown) are formed by sawing of chip 112 from a larger wafer of single crystal silicon, such sawing typically being performed after hole 118 is formed by etching, so that many holes such as 118 can be formed simultaneously before the silicon wafer is diced to form many chips such as chip 112.

Figure 3A:
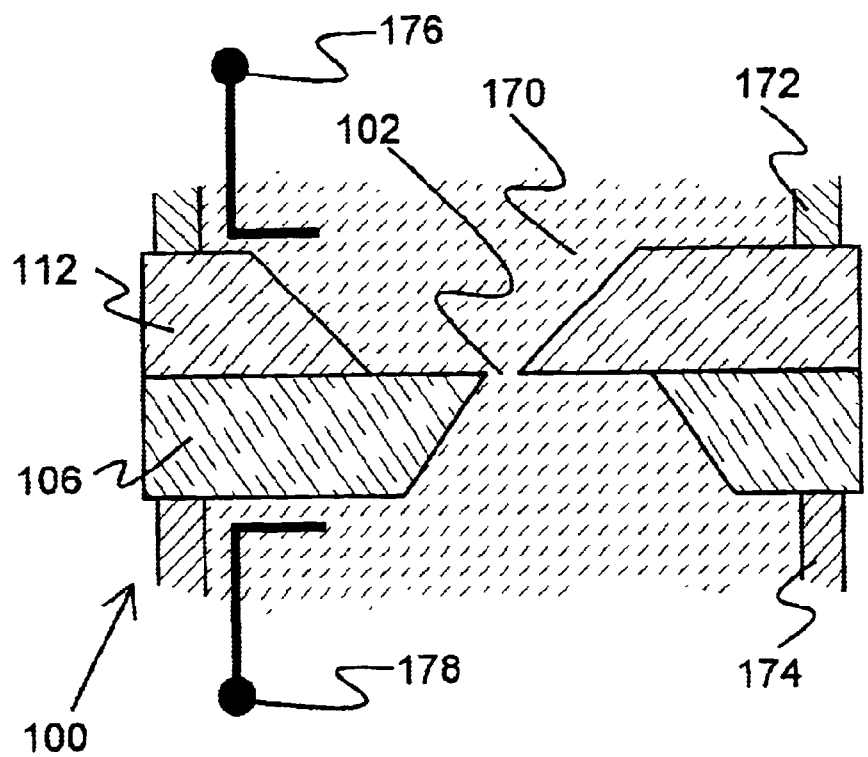
FIGS. 3a–3c illustrate successive changes in the size of the adjustable nanopore.
Figure 3B:
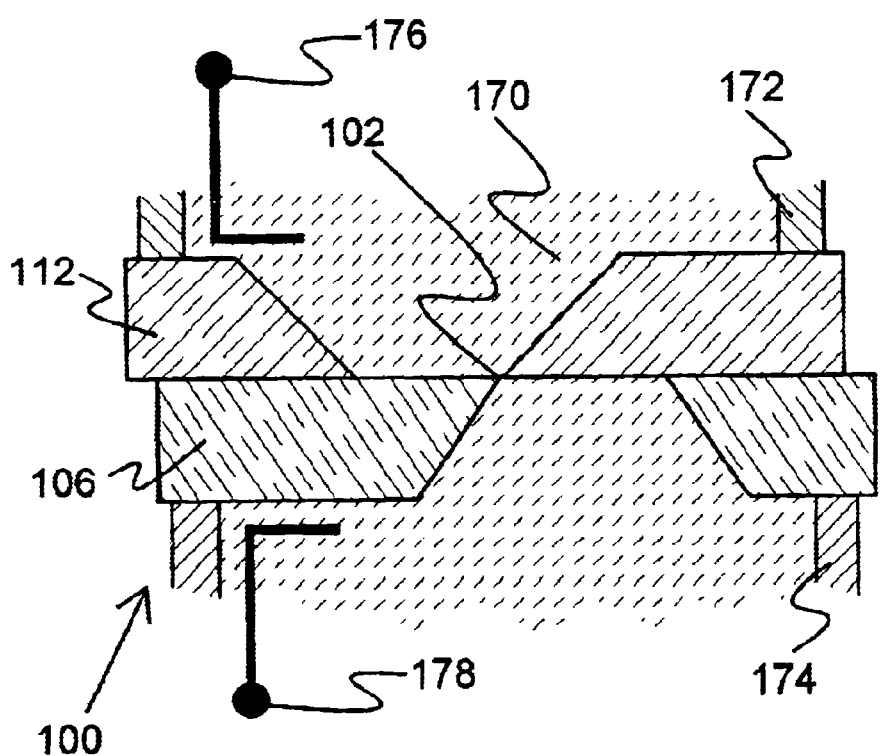
Figure 3C:
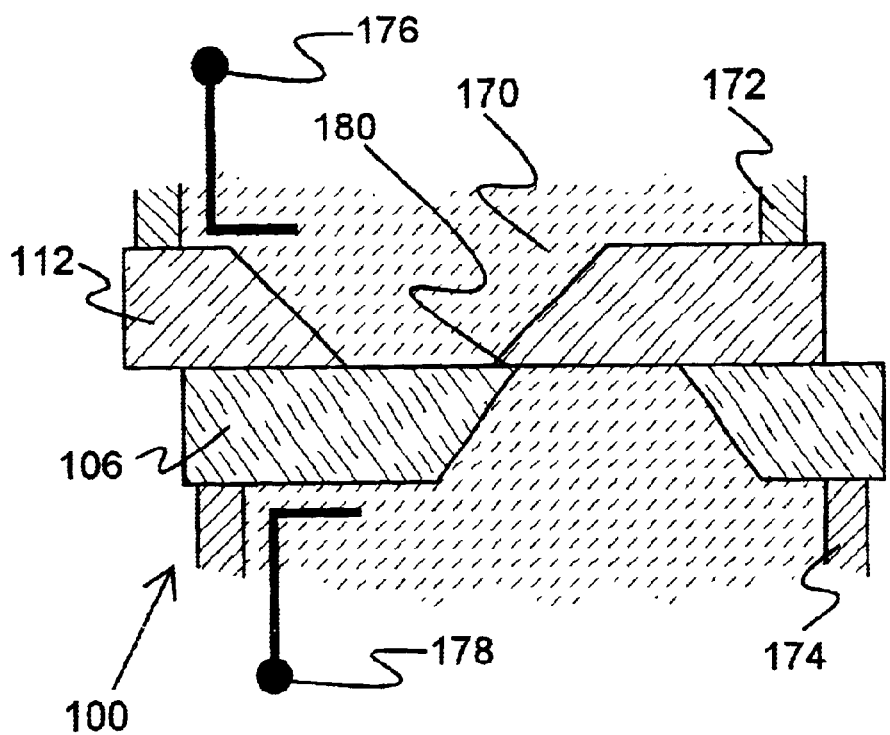

FIGS. 3a, 3b, and 3c illustrate successive changes in the size of the adjustable nanopore. Ionic conducting liquid 170 fills a volume including nanopore 102 and is contained by walls 172 and 174. Electrodes 176 and 178 make contact with liquid 170 and allow monitoring of electrical current passing through hole 102. In FIG. 3a, the hole 102 is open. In FIG. 3b, the hole 102 has closed to zero area as chip 112 slides to the left with respect to chip 106. In FIG. 3c, the hole 102 is completely closed, so that any electrical current between electrodes 176 and 178 must pass as leakage current along interface 180. The size of the pore may thus be monitored by monitoring the ionic current through the pore.

The leakage current depends to some extent on the surface roughness of the two surfaces 130 and 136 at interface 180. Such roughness can be controlled in typical silicon fabrication technology to a level on the order of 0.16 to 0.19 nm RMS (see, for example, C. Cowache, et al, "Evaluation of advanced pre-gate cleanings", Cleaning Technology in Semiconductor Device Manufacturing. Proceedings of the Sixth International Symposium, *Electrochemical Society Proceedings*, Vol. 99–36, pp. 59–68 (2000), also available at the Akrion web site at http://www.akrion.com/apex/tech articles.html), which roughness is much less than, for example, the 2 nm width of a DNA molecule or the 0.72 nm diameter of a hydrated sodium ion (J. N. Israelachvili, supra, p. 55), so that it is not unreasonable to expect that leakage current along the interface might be reduced completely to zero.

The sequence of drawings in FIGS. 3a–3c also apply to using the adjustable nanopore in a nanotome mode which can cut molecules, or objects larger than molecules, extending through the nanopore. Closing the pore while an object extends through the pore creates a shearing force analogous to that exerted by a pair of scissors cutting a string. As can happen when using a scissors to cut a string, it may happen that the molecule or other object to be cut can slip into the interface between the blades formed by the corner and the edge. In this instance, continuing to move the corner with respect to the edge past the closing point of the nanopore, as in FIG. 3c, will ultimately create enough drag along the length of the trapped portion of the molecule or other object to cut it into two pieces. An alternate embodiment, also depicting a nanotome, is described below with reference to FIGS. 5a–5b.

The sequence of drawings in FIGS. 3a–3b also apply to using the adjustable nanopore in a nanotweezer mode which can capture molecules, or objects larger than molecules, extending through the nanopore. Closing the pore while an object extends through the pore creates a holding force analogous to that exerted by a tweezer holding a string. An alternate embodiment, also depicting a nanotweezer, is described below with reference to FIGS. 5a–5b.

Figure 4A:
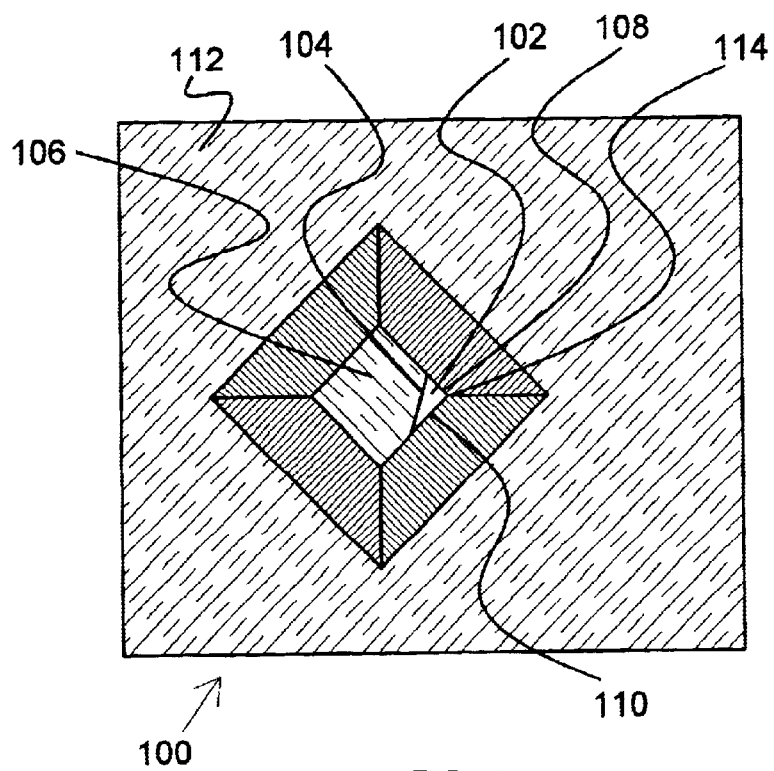
FIGS. 4a–4b illustrate adjustment of the nanopore to an asymmetric position, so as to provide capability of discriminating between chiral molecules, wherein in FIG. 4a, the bottom chip is rotated 15° clockwise with respect to its position in FIG. 1b and wherein in FIG. 4b, the bottom chip is rotated 15° counterclockwise with respect to its position in FIG. 1b.
Figure 4B:
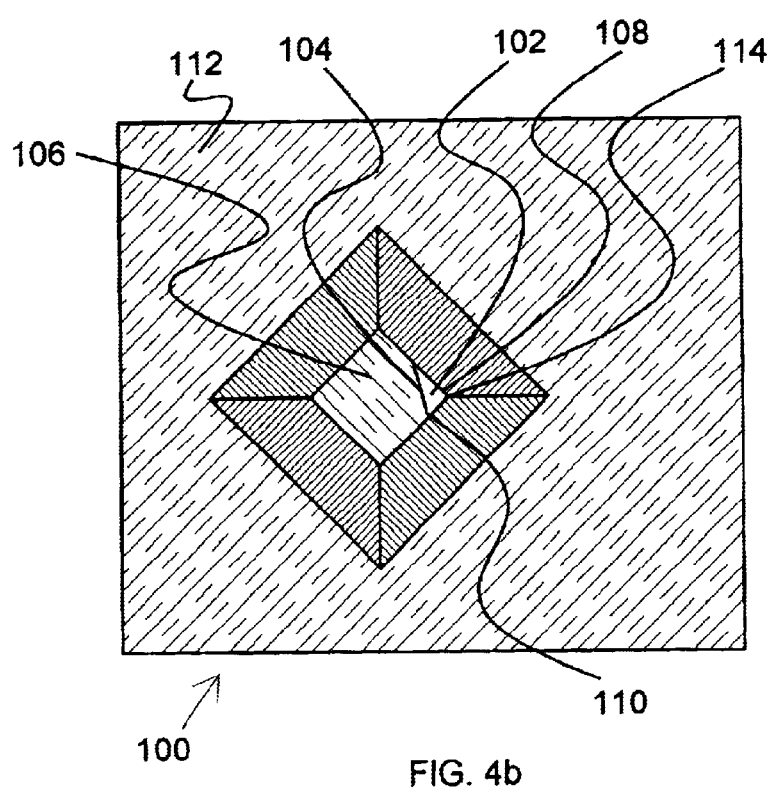

Advantageously, the adjustable nanopore 100 can be adjusted to be asymmetric and so can have some capability of discriminating between chiral molecules. FIGS. 4a–4b illustrate two plan views of the same adjustable nanopore 100 as shown in FIG. 1b. In FIG. 4a, the bottom chip 106 has been rotated 15° clockwise with respect to its position in FIG. 1b, and in FIG. 4b, the bottom chip 106 has been rotated 15° counterclockwise with respect to its position in FIG. 1b. Rotation of one chip relative to the other so as to vary the angle of a triangular aperture may be performed with an angular orientation mechanism as part of the actuators.

Thus, in FIG. 4a, nanopore 102 has a cross-sectional shape with an asymmetry which is a mirror image of the cross-sectional shape of pore 102 in FIG. 4b. In FIG. 1b, the cross-sectional shape of pore 102 is seen to be an isosceles triangle. By using the three configurations of FIGS. 1b, 4a, and 4b, an investigator has the possibility of distinguishing among molecules which are chiral, that is, molecules which are not symmetrical with their mirror image.

Through-holes 116, 118 are etched in each chip 106, 112, respectively, by orientation-dependent etching which results in a pyramidal-frustrum-shaped hole with edges and corners which are atomically sharp, or nearly atomically sharp. Such etchants are well-known, and comprise, for example, tetramethyl ammonium hydroxide (TMAH) in water for etching holes in silicon chips wherein the surfaces are perpendicular to <100> crystalline directions in the single crystal substrate. Other similar etchants include but are not limited to ammonium hydroxide in water, sodium hydroxide in water, a mixture of ethylenediamine and pyrocatechol in water, potassium hydroxide in water, a mixture of potassium hydroxide and isopropanol in water, a mixture of potassium hydroxide and aluminum in water, cesium hydroxide in water, hydrazine in water, and rubidium hydroxide in water.

For example, a 20% solution by weight of TMAH in water etches [100]-oriented silicon (that is, a silicon wafer oriented with its major surfaces perpendicular to a <100> crystal direction) at a rate of approximately 1.1 $\mu$m per minute, and does not appreciably etch thermally grown silicon dioxide on silicon, so that silicon dioxide can be used as a masking material to define the square hole to be etched through the silicon chip. Other masking materials including, but not limited to, silicon nitride and deposited metal layers can also be used. Other silicon orientations such as [110]-oriented wafers and [111]-oriented wafers can also be used, but [100]-oriented wafers are the most commonly available and cheapest, and so are preferable. In [100]-oriented silicon, the through-holes 116, 118 typically have a wider portion at the upper surface 132, 134, respectively, and a narrower portion at the lower surface 136, 130, respectively, of the silicon chips 106, 112. The monocrystalline substrates of germanium and diamond may also employ the same crystallographic wafer orientations, namely, the major surface of the substrate being oriented substantially perpendicular to the [100] direction, the [110] direction, or the [111] direction.

Typically, there is some finite etch rate of the silicon chip in orientation dependent etches in the <111> directions, so that some undercutting of the masking material occurs during orientation dependent etching, leaving overhanging lips of masking material after etching which would interfere with the operation of the adjustable nanopore. Such lips can easily be removed. For example, a lip of silicon dioxide can be removed by etching in a hydrofluoric acid solution, which etches silicon dioxide but does not etch silicon.

The formation of a sharp edge by orientation-dependent etching is the preferred method for embodying the present invention, but other methods of fabricating a sharp edge are available. As one alternative, a sharp edge may be formed by cleaving, chipping, spalling, flaking, exfoliating, or knapping a single-crystal material including, but not limited to, silicon, germanium, diamond, and quartz. As another alternative, a sharp edge may be formed by cleaving, chipping, spalling, flaking, exfoliating, or knapping a polycrystalline material in such a manner that an edge of a single crystal within the polycrystalline material is exposed. As a further alternative, a sharp edge may be formed in an amorphous material such as polished glass by cleaving, chipping, spalling, flaking, exfoliating, or knapping so as to leave a sharp edge adjacent to a polished face of the amorphous material. Other alternative methods will occur to those skilled in the art.

Likewise, the formation of a sharp corner by orientation-dependent etching is the preferred method for embodying the present invention, but other methods are available. As one alternative, a sharp corner may be formed by cleaving, chipping, spalling, flaking, exfoliating, or knapping a polycrystalline material in such a manner that a groove bounded by two single crystals within the polycrystalline material, and intersecting a polished surface of the polycrystalline material, is formed. Other alternative methods will occur to those skilled in the art.

After holes are etched completely through the silicon wafer, the wafer can be diced with a mechanical saw into individual chips.

During the time between etching and dicing, and in the time period during and after dicing, the fresh silicon surfaces of a silicon chip tend to oxidize in water and in room air to a thickness less than approximately 2 nanometers (nm), which can lead to nanometer-scale changes in the morphologies of edges and corner of the etched hole.

If desired, after dicing each chip can then be exposed for a short time to an etchant such as TMAH to create freshly-etched silicon surfaces in the through-hole.

The masking thin film can then be stripped from the chip, leaving surfaces, edges, and corners with a high degree of perfection. Such surfaces, edges, and corners again tend to oxidize in room air, so it can be advantageous to immediately transfer the freshly-stripped chip to a non-oxidizing environment such as dry nitrogen.

After the masking material is removed, the result is a through-hole with acute edges which are atomically sharp, or nearly so, and with concave corners, or grooves, which are atomically sharp, or nearly so. The tetrahedral radius of a silicon atom in a crystal is 0.118 nm (see, e.g., *VLSI Fabrication Principles* by S. K. Ghandi, Wiley-Interscience, p. 5 (1983) ISBN 0-471-86833-7) and this radius is a lower bound on the sharpness of such an edge or corner. However, atomically sharp edges and grooves are energetically unfavorable and tend to remodel due to surface oxidation in room-temperature air, or due to atomic diffusion, or both, so that some further radiusing of edges and grooves may be expected to occur. Oxidation of silicon occurs in air or water at room temperature to thicknesses as great as 2 nm.

The combination of oxidation and remodeling can be expected to leave the etched holes with edges and corners having radii of curvature between 0.118 and 100 nm. From prior art experience with sharpened tips for STMs and AFMs which can have radii of curvature on the order of 2 nm to 10 nm, it is expected that the edge and corner regions of the present invention can have radii of curvature of 2 to 10 nm, and possibly less, after the use of the above fabrication techniques. See, for example, V. Milanovic et al, "Deep Reactive Ion Etching for Lateral Field Emission Devices", *IEEE Electron Device Letters*, Vol. 21, no. 6, pp. 271–273 (June 2000). It is reasonable to expect such edge and corner radii to be on the order of 10 nm, also reasonable to expect such radii to be as small as 2 nm, and not unreasonable to expect radii below 2 nm. Thus, the minimum distance from an edge to a corner is less than 100 nm, preferably less than 10 nm, more preferably less than 2 nm, and most preferably less than 1 nm.

If desired, an insulating layer (not shown) of one or more materials including, but not limited to, silicon dioxide and silicon nitride may be formed by chemical reaction on the surfaces of the silicon chips 106, 112. Alternatively, an insulating layer (not shown) of one or more materials including, but not limited to, silicon dioxide, silicon nitride, silicon carbide, diamond, or diamond-like carbon may be deposited on the surfaces of the silicon chips 106, 112, by deposition techniques including, but not limited to, evaporation, sputtering, chemical vapor deposition, and ion implantation, or insulating layers may be both formed by chemical reaction and deposited. If desired, the formed or deposited layers may be arranged so that they create a characteristic radius of curvature at the corners of the holes 116, 118, or so that they increase the sharpness of the corners of the holes, or provide some combination of both radius and sharpness along different directions or at different locations. For example, oxidation sharpening of edges and points is well-known, and the use of oxidation to increase the sharpness of the angle of a groove is also known; see, e.g., R. B. Marcus et al, "The Oxidation of Shaped Silicon Surfaces", *The Journal of the Electrochemical Society*, Vol. 129, no. 6, pp. 1278–1282 (1982); R. B. Marcus et al, "Formation of silicon tips with <1 nm radius", *Applied Physics Letters*, Vol. 56, no. 3, p. 236–238 (1990); and T. S. Ravi et al, "Oxidation sharpening of silicon tips", *Journal of Vacuum Science and Technology*, Vol. B9, no. 6, p. 2733–2737 (1991). Oxidation sharpening has been used to prepare sharp tips for STMs and AFMs; see, e.g., R. B. Marcus et al., *Applied Physics Letters*, supra, and can be applied to edges in the present invention if desired. In oxidation sharpening of a tip or edge, the oxide is removed from the part to be sharpened after oxidation is performed, leaving a sharpened point or edge exposed. In oxidation sharpening of a groove, the grown oxide is left in place to comprise the sharpened groove at the exposed oxide surface.

To prevent stiction and reduce friction, the contacting surfaces 136, 130 of the silicon can be coated with an anti-stiction layer of a material or materials including, but not limited to, diamond, diamond-like carbon, silicon carbide, a self-assembled monolayer such as dichlorodimethylsilane, octadecyltrichlorosilane, dodecyltrichlorosilane, or perfluorodecyltrichlorosilane, various alkanethiols, molecular films based on the free radical reaction of a primary alkene (e.g., 1-octadecene, $C_{16}H_{33}CH=CH_2$) with hydrogen-terminated silicon, or the like. For a review of such stiction reduction techniques see, for example, the web site at http://stiction.cchem.berkeley.edu/papers.html, which includes a citation to "Dichlorodimethylsilane as an anti-stiction monolayer for MEMS: a comparison to the octadecyltrichlorosilane self-assembled monolayer", W. R. Ashurst et al, *Journal of Microelectromechanical Systems*, Vol. 10, No. 1, pp. 41–49 (March 2001). In order to keep the edge and the corner of the nanopore as sharp as possible, self-assembled monolayers are preferable to thicker deposited layers.

It will be appreciated by those skilled in the art that even when anti-stiction layers are used, other structural features acting to reduce stiction may be desirable. One such structural feature is a set of recessed regions (not shown), formed in selected regions in one or both of surfaces 130 and 136, by means such as chemical etching. Such recessed regions act to reduce the total bearing area between surfaces 130 and 136 and so act to reduce the total stiction force.

After the edges, grooves, and surfaces of the silicon chips are prepared as desired, the two surfaces of the silicon chips 106, 112 containing the narrower ends of the through-holes 116, 118, namely, surfaces 136, 130, are placed in contact so that a continuous path through the through-holes exists, thereby defining aperture 102.

To one silicon chip, say, chip 112, the piezoelectric actuators 120, 122, 124, are attached via block 126, with spring loading (not shown) along each axis to prevent hysteresis during positioning. Alternatively, it may be advantageous to have some hysteresis in the positioning mechanism, so that the pore, once positioned with an opening of a given width, will maintain that width unless the positioning signal departs from a "dead band" characteristic of the hysteresis.

The preferred method of fabricating many adjustable nanopores in a cost-effective manner is to fabricate through-holes using orientation-dependent etching of silicon wafers in TMAH, then dice the wafers into individual chips to which glass tubes are attached, then attach a piezoelectric positioner to at least one chip of each pair of chips to be used to form a nanopore, then coat at least one of the sliding surfaces of each pair of chips with the anti-stiction layer. However, many variations on this preferred method are possible without departing from the spirit and scope of the present invention.

Following assembly, the device 100 is then immersed in a desired liquid ionic conductor 170 as shown in FIGS. 3*a*, 3b, and 3c, and an ionic current is established through the aperture 102 by applying a voltage to electrodes 176 and 178 on opposite sides of the aperture. Walls 174 and 172 comprising, for example, a glass or a polymer may be attached to one or more of lower and upper surfaces 132 and 134 by means including, but not limited to, adhesives, clamps and gaskets, and anodic bonding in order to isolate solution 170 from the surroundings.

Along one positioning axis, called for convenience the x-axis 128, the width of the aperture 102 is reduced until the ionic current either goes to zero or exhibits a change in slope indicating that the cross sectional area of aperture 102 has been reduced to zero so that the only remaining conduction is due to leakage current along the interface 180 between surfaces 130 and 136.

The x-axis positioning 128 is then backed off until the ionic current rises to some desired level indicating that the aperture 102 has a desired finite area.

The two silicon chips 106, 112 may then be clamped in place, if desired, or may be bonded together if desired, or the positioners 120, 124, and 126 may be placed in an electronic feedback loop arranged so as to maintain constant ionic current over some frequency range, or the drive signals for the positioners 120, 124, and 126 may be set to a constant level to hold the two chips 106, 112 in a constant relative position. Alternatively, the feedback loop may be used to control the size of the pore. Electric feedback loops or computer controlled feedback loops may be used, as appropriate.

If desired, the size of the resulting aperture 102 may be further characterized by removing the ionic solution 170, placing the device 100 in vacuum, and using evaluations means such as transmission electron microscopy or ionic transmission.

Optionally, light transmission instead of ionic current may be used to characterize the desired aperture size. In such a case, one or more surfaces of the silicon may be metallized to make it opaque to transmitted light so that light transmission through the aperture can be accurately monitored.

The resulting aperture 102 in the nanopore 100 may be used as desired in characterizing long-chain molecules which pass through the aperture. Such molecules can include, but are not limited to, molecules, molecular complexes, and supramolecular complexes, such as, but not limited to, polynucleotides, polynucleosides, polypeptides, polysaccharides, and lipids. For an overview of such molecules see, for example, Bruce Alberts et al, *Molecular Biology of the Cell*, Third edition, Garland Publishing, New York, pp. 89–138 (1994) ISBN 0-8153-1619-4. For example, a typical double helix molecule of DNA has a negative charge in an ionic aqueous solution, and has a width of approximately 2 nm and a length of thousands of nanometers or more, with a double helix spiral shape which twists through a full turn in a distance along the molecule's length of approximately 1 nm. An aqueous ionic solution can be prepared containing many copies of such a DNA molecule by techniques such as the well-known polymerase chain reaction (PCR). The maximum initial width dimension of the adjustable nanopore can be set to a value slightly greater than 2 nm, and an ionic current tending to pull negative charges through the nanopore 102 can be established. The ionic current will occasionally pull a DNA molecule into the pore. If the pore is used in a mode such that a constant control signal is applied to the positioner or positioners to keep the pore width constant, then the result of a DNA molecule entering the pore is that current through the pore is reduced in a manner similar to that seen in the teachings of U.S. Pat. No. 5,795,782. If the width of the pore is then reduced while the reduced current indicates that the DNA molecule is passing through the pore, the molecule can be trapped by the pore acting as a nanotweezer, or can be cut by the pore acting as a nanotome.

As another example, a polypeptide comprising hundreds or thousands of amino acids folded to form a protein molecule will substantially block the adjustable nanopore when the minimum dimension of the nanopore is set to 2 nm and will substantially reduce ionic current through the pore. The minimum dimension of the pore may then be increased to a size which allows the blocking protein molecule to pass through the pore, allowing ionic current to increase, and the size of the pore at which the protein molecule is able to pass through then gives an indication of the size of the protein molecule.

The adjustable nanopore permits much more data to be gathered on molecules than, for example, does the use of the naturally-occurring alpha-hemolysin channel in a lipid membrane such as, for example, in the work reported by W. Vercoutere et al, "Rapid discrimination among individual DNA hairpin molecules at single-nucleotide resolution using an ion channel", *Nature Biotechnology*, Vol. 19, no. 3, pp. 248–252 (2001). For example, consider a long-chain molecule containing two wider portions at two points along its length. Such a molecule could be, for example, a single-stranded RNA molecule with, at two points along its length, RNA hairpins in which the RNA molecule loops back upon itself to form local hydrogen bonds which form a double strand region, making the RNA molecule wider in the hairpin regions than in the linear single-stranded region. If one end of the single-stranded RNA molecule enters the adjustable nanopore while the minimum width of the nanopore is set to slightly less than 2 nm, the molecule will reduce the ionic current through the pore while the molecule begins to transit through the pore. When the first hairpin region encounters to pore, the molecule will stop because the width of the pore is smaller than the width of the hairpin, and the ionic current through the pore will be further reduced. The experimenter then knows that the hairpin region is at the nanopore. The width of the adjustable nanopore can then be increased, allowing the hairpin to pass through. Immediately afterwards the width of the nanopore can be decreased to its initial value of less than 2 nm, allowing the further passage of the single-strand region between the two hairpins but stopping the molecule again when the second hairpin is encountered. The experimenter now has a molecular preparation of single stranded RNA between the two hairpin regions trapped within the nanopore, and he/she can reverse the applied electrical potential applied to the solution to make the single stranded region transit to pore in a reverse direction until it again encounters the first hairpin. The trapped region of single-stranded RNA can thus be shuttled back an forth within the nanopore as many times as desired, and the ionic current through the nanopore can be measured as many times as desired, to build up a mass of data on the single stretch RNA. While the molecule remains trapped, the angle of the nanopore can be adjusted among the positions of FIGS. 1b, 4a, and 4b to evaluate the chiral properties of the molecule.

Similar strategies of trapping a narrow region of a molecule bounded between two wider regions so that it can be shuttled back and forth through the adjustable nanopore can be applied to other molecules, for example to a stretch of double-stranded DNA bounded by two wider regions created by proteins bound to the grooves of the double-stranded DNA using one or more DNA-binding protein motifs including, but not limited to zinc finger motifs, helix-turn-helix motifs, beta-sheet motifs, leucine zipper motifs, and helix-loop-helix motifs. For a discussion of such DNA-binding protein motifs see, for example, Bruce Alberts et al, *Molecular Biology of the Cell*, supra, pp. 408–413.

Advantageously, once such a trapped molecular preparation is prepared, both the width and the angular configuration of the nanopore may then be adjusted while the molecule remains trapped, such adjustments occurring within limits which neither free the trapped molecule nor cleave it, so that the ionic current flowing past the trapped molecule can be characterized for a range of different pore sizes and shapes.

From the foregoing, it will be readily appreciated that the adjustable nanopore can be adjusted to a first width that is small enough to block passage of a molecule at a first point in its structure. The width can then be increased to a second width sufficient to permit the molecule to begin to proceed again through the nanopore. By monitoring the increasing width of the nanopore to the second width to the extent that it is just sufficient to allow the molecule to continue through the nanopore, further information about the structure of the molecule may be obtained. Where the molecule has a long chain structure, after the molecule is permitted to proceed again through the nanopore, the width of the nanopore may be subsequently decreased to a third width while the molecule is still proceeding through the nanopore. The third width may be sufficiently small to subsequently block the passage of the molecule at a second point along its structure. The direction and magnitude of the ionic current can be varied to provide further information about the structure of the molecule.

As mentioned above, the nanopore of the present invention can be used to cleave molecules ("nanotome"). For long chain molecules, the nanopore can be employed to block the passage of the molecule at a desired wide location along the molecule prior to cleaving the molecule, utilizing the teachings above. Further, the nanopore can be used to trap a narrow section of the molecule situated between two wider sections of the molecule prior to cleaving. For purposes of description herein, the passage of a molecule is said to be blocked if motion of the molecule through the nanopore in one direction is stopped by the width of the molecule in relation to the width of the nanopore. When the passage of the molecule is blocked, a portion of the molecule may extend through the nanopore. A molecule is said to be trapped if a narrow portion of the molecule situated between two wider sections of the molecule extends through the nanopore, and the width of the nanopore is small enough to block the passage of each of the two wider sections of the molecule.

As also mentioned above, the nanopore of the present invention can be used to grab molecules ("nanotweezer"). The nanopore can be used in the same way as described above with regard to the nanotome to block the passage of the molecule or to trap a section of the molecule.

Figure 5A:
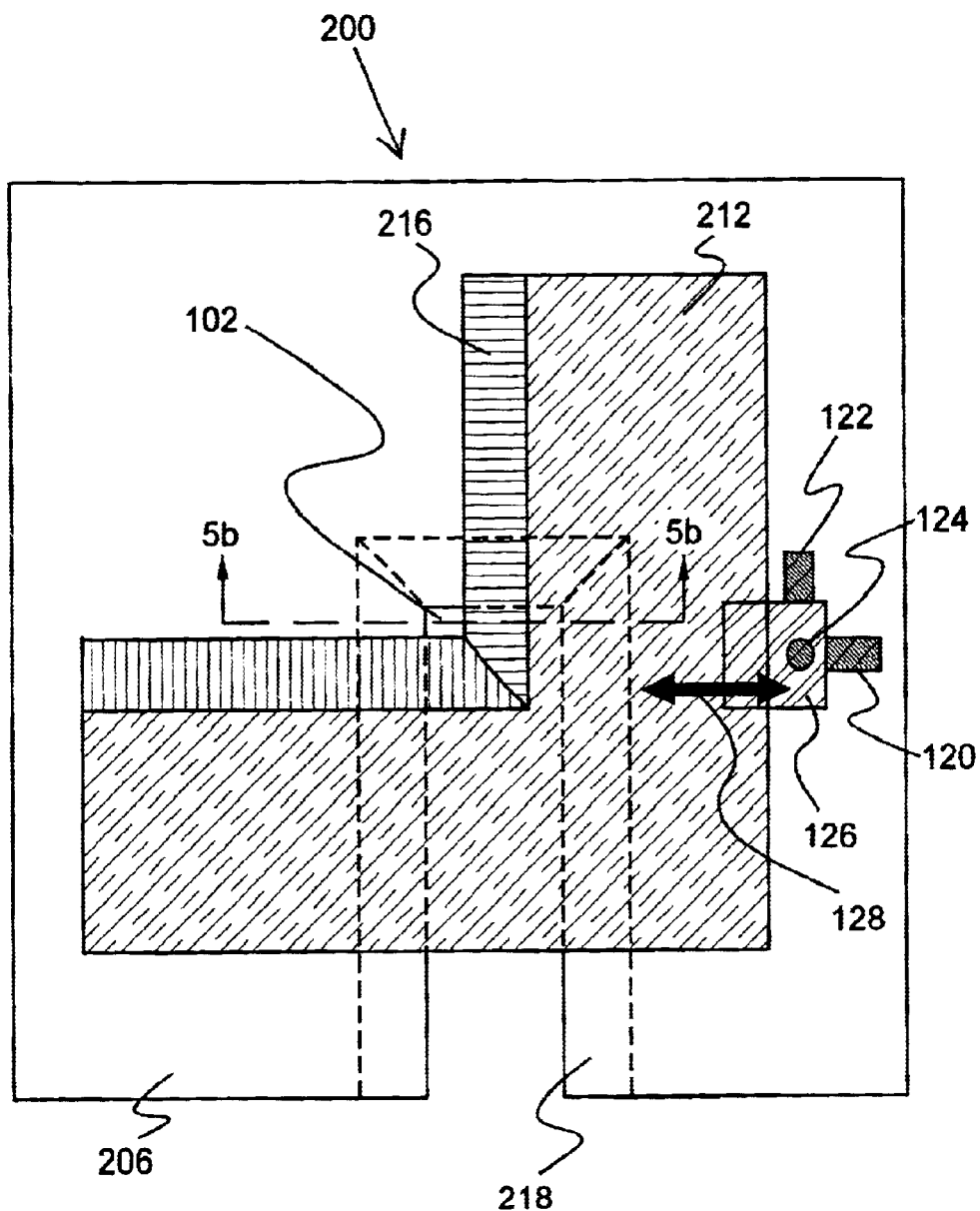
FIG. 5a is a top plan view, showing two overlapping corners in two silicon pieces, forming an adjustable aperture and depicting a second embodiment, called a nanotome.
Figure 5B:
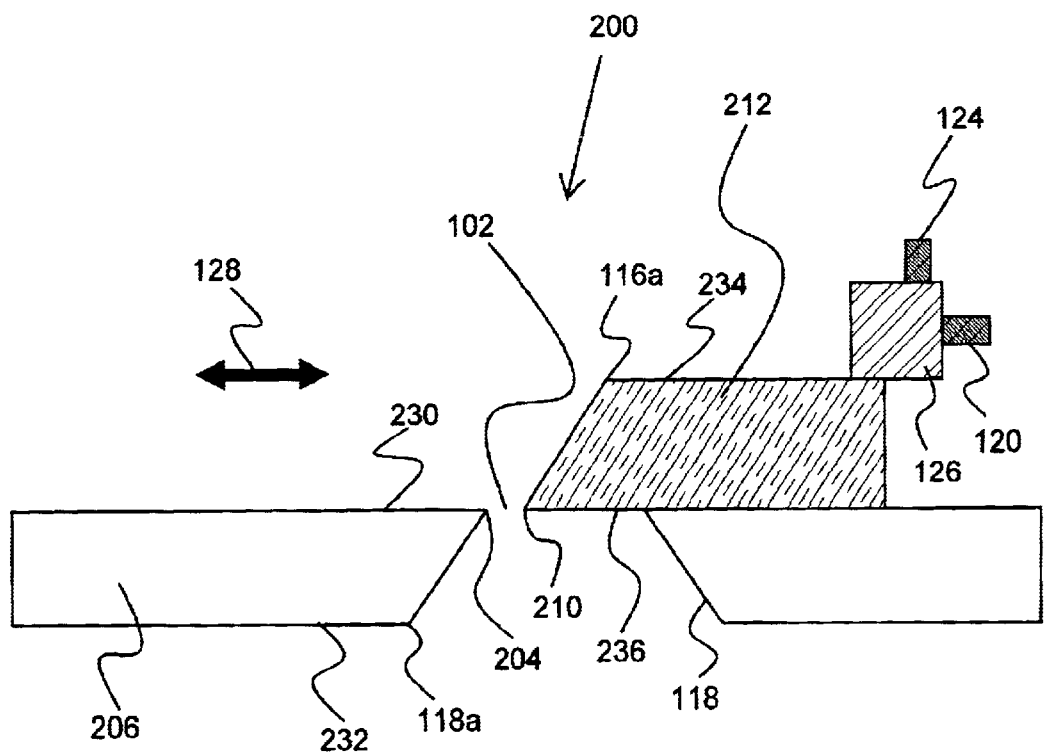

Also optionally, corners or notches 216, 218 may be used in one or both pieces of silicon 206, 212 instead of through-holes, as shown in FIGS. 5a and 5b, to facilitate the capture of stretched long-molecular-chain preparations and to facilitate use as a nanotome or nanotweezer 200. The aperture 102 that is formed functions as described above, and is adjustable with piezoelectric actuators 122, 124, 126, as described above.

FIG. 1b, discussed above, illustrates the combination of a corner 114 and an edge 104, which forms a triangle. Alternatively, the through-holes 116, 118 could be oriented such that two opposing corners formed the adjustable pore 102, which has a cross sectional shape of a square, more generally of a rectangle, or a more generally of rhombus. FIG. 5a depicts such a configuration. Likewise, the corner piece 216 in FIG. 5a could be oriented such that it moved relative to a straight edge of corner piece 218, thereby also forming a triangle.

The triangle configuration for the nanopore, the nanotome, and the nanotweezer are preferred. However, the square, rectangle, or rhombus configuration for each of the nanopore the nanotome, and the nanotweezer is an alternative configuration that may find some use. For example, if the nanopore initially has a triangular aperture, and if a second corner, also having a radius of curvature less than 100 nm, is adjacent the sharp edge forming one side of the triangular aperture, then the position of the first corner can be adjusted with respect to the second corner so that the triangular cross section can be changed to a four-sided rhomboidal cross section, which can have additional utility in determining the geometrical characteristics of the molecule passing through the nanopore, or trapped by the nanopore in a manner allowing reciprocal motion of the molecule with respect to the nanopore to be accomplished. As above, an angular orientation mechanism can be provided to change the relative angle of the second corner to the first corner so as to vary the angles of the rhomboidal aperture thus formed.

Optionally, the aperture size of adjustable nanopore 102 may be varied actively during use in some applications, such as those discussed above, and the angular orientation of the two substrates comprising the nanopore may be varied actively during use in some applications, such as those discussed above.

While silicon semiconductor chips have been disclosed herein, the same teachings of the present invention may be employed with respect to other orientations of silicon substrates as well as other materials, including but not limited to those noted above.

Figure 6A:
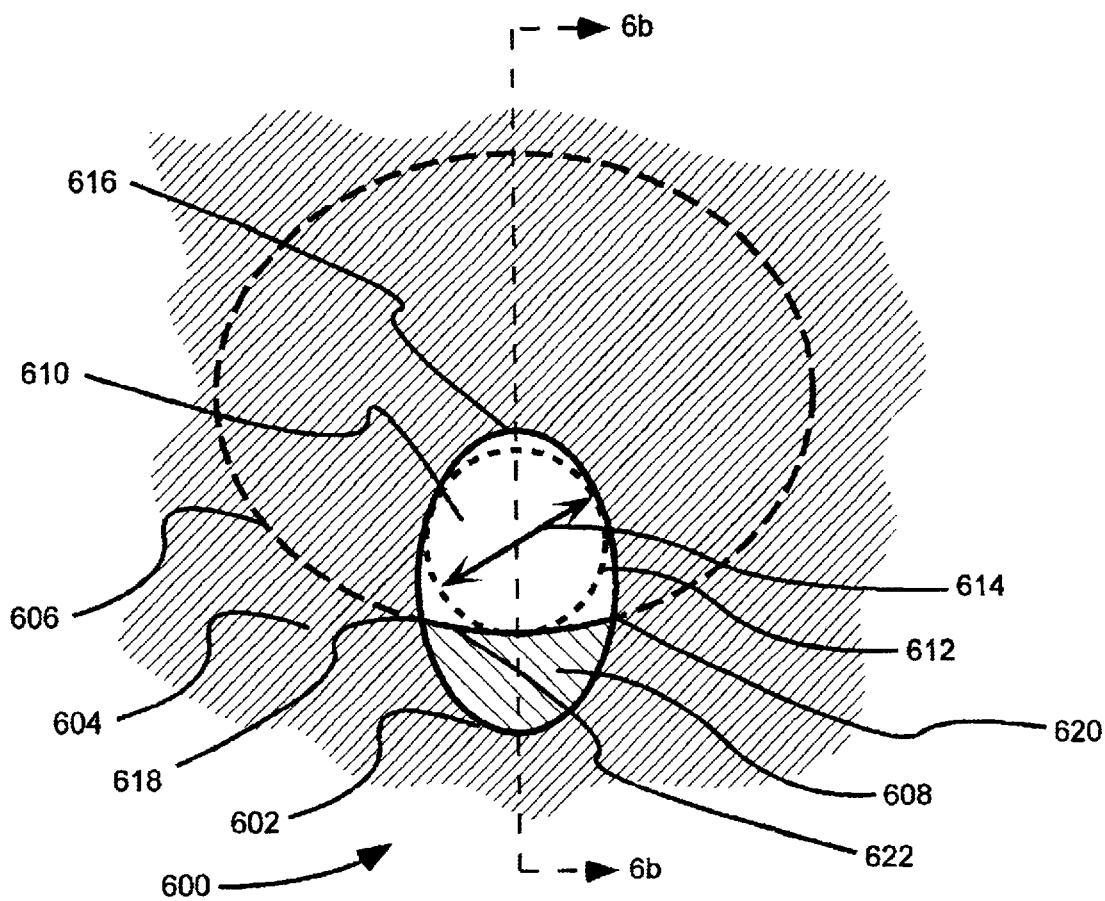
FIG. 6a is a top plan view of an alternative embodiment in which two through-holes in two taut membranes overlap to form an adjustable nanopore.
Figure 6B:
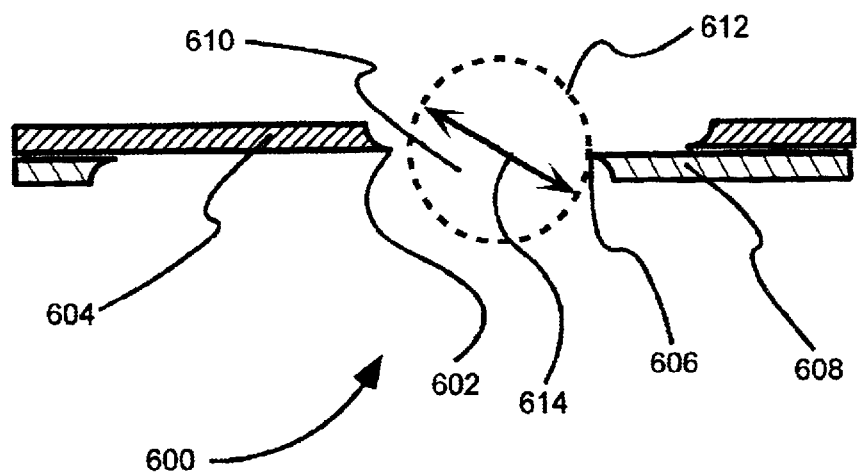

As one example, FIGS. 6a–6b illustrate an alternative embodiment 600 of the invention. Through-hole 602 exists in membrane 604. The through-hole 602 may be formed, for example, by sculpting with an argon ion beam in a membrane 604 of silicon nitride as described in J. Li et al, "Ion-beam sculpting at nanometer length scales", *Nature*, Vol. 412, pp. 166–169 (Jul. 12, 2001). A similar hole 606, formed, for example, by the same techniques, exists in membrane 608, which membrane can also be made of silicon nitride. The two membranes, which can for example be supported on frames (not shown) of single-crystal silicon, are placed in contact or near contact, and hole 602 is placed to intersect an edge of hole 606 to form an arched opening 610 through which a sphere 612 of diameter 614 may pass. The crown of the arch is a point 616, the springer points of the arch are at points 618 and 620, and the base of the arch is formed by the edge portion 622 of through-hole 606.

Figure 7A:
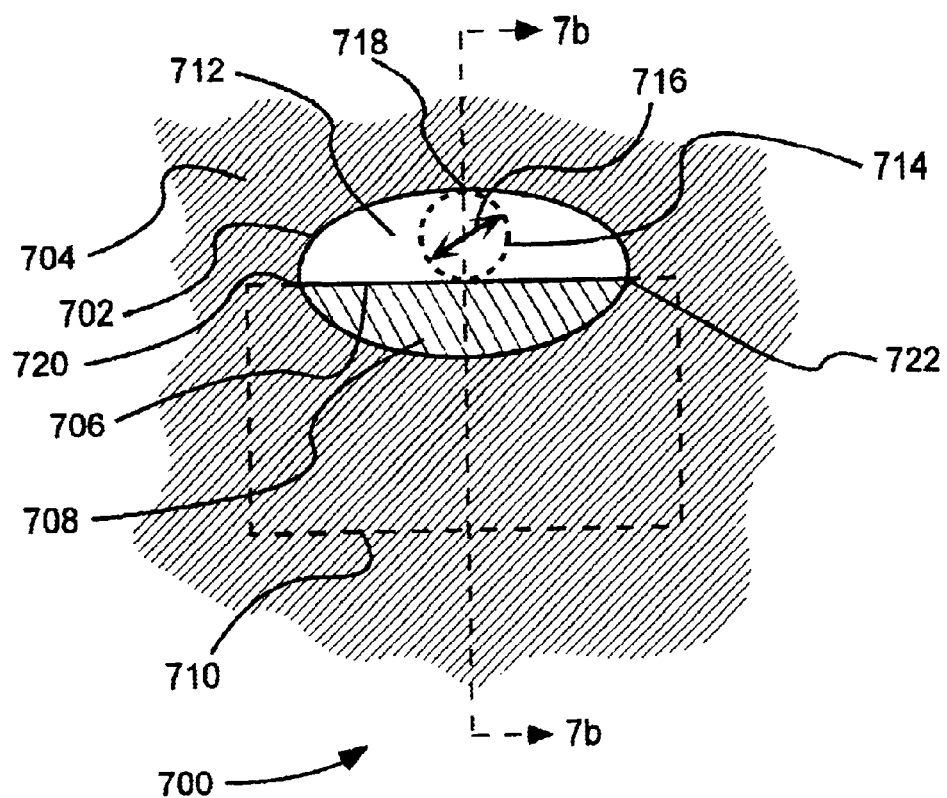
FIG. 7a is a top plan view of an alternative embodiment in which a through-hole in a taut membrane and an edge of a body carried on a cantilever combine to form an adjustable nanopore.
Figure 7B:
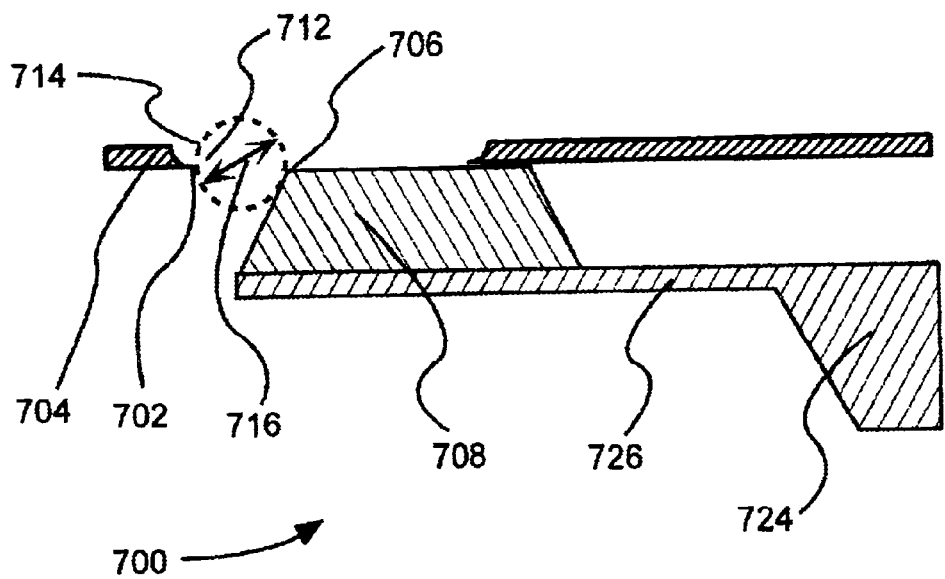

Another alternative embodiment 700 of the invention is illustrated in FIGS. 7a–7b. Hole 702 in membrane 704 is formed by means similar to those used to form hole 602. Edge 706 of body 708 is part of edge 710 which bounds a planar surface of body 708. Edge 706. intersects hole 702 to form an arched opening 712 through which a sphere 714 of diameter 716 may pass. The crown of the arch is point 718, the springer points of the arch are points 720 and 722, and the base of the arch is formed by edge 706. Body 708 is formed by means of, for example, chemical vapor deposition, photolithography, and etching on a surface of substrate 724 which is later etched to form cantilever 726. Cantilever 726 may contain sensing means (not shown), such as piezoresistive sensors to monitor the contact force between membrane 704 and body 708. Such sensing means are well known to those skilled in the art of atomic force microscopy. Cantilever 726 may contain actuation means (not shown), such as piezoelectric actuators to move body 708 in three directional axes and a rotational axis with respect to membrane 704. Such actuators have previously been used in cantilevers for scanning tunneling microscopy, for example, T. R. Albrecht et al, "Microfabrication of integrated scanning tunneling microscope", *Journal of Vacuum Science and Technology,* Vol. A8(1), pp. 317–318 (January/February 1990).

Variations on the structures described above may occur to those skilled in the art without departing from the scope and spirit of the present invention. For example, other cantilever structures such as those employed in STM and AFM apparatus may be incorporated into the structure of the present invention, and other flexible structures comprising springs, beams, and flexures may be incorporated into the structure of the present invention. Sensing means such as piezoelectric sensors, optical sensors, and other types of sensors may be incorporated into the present invention to aid in detecting the relative positions of the structural components of the present invention, and to aid in detecting the force with which such structural components bear upon one another. Layers such as elastomeric layers and polymeric brushes may be incorporated, for example between surfaces 130 and 136 of embodiment 100, for purposes such as elastically filling in local surface roughness.

INDUSTRIAL APPLICABILITY

The nanopore, nanotome, and nanotweezer of the present invention are expected to find use in a variety of applications, including separation of molecules, characterization of molecules, cutting of molecules, and capturing of molecules.

What is claimed is:

1. An adjustable nanopore comprising:
    a first substrate having a sharp concave first corner therein, the first corner being bounded by a first surface of the first substrate, the first corner having a radius of curvature less than 100 nm;
    a second substrate having a second edge bounded by a second surface of the second substrate;
    wherein the first surface is placed in contact with the second surface so as to create a pore bounded by the first corner and the second edge; and
    an adjustable mechanism for increasing and reducing the minimum distance from the second edge to the first corner in a range including a minimum distance less than 100 nm.

2. The nanopore of claim 1 wherein the minimum distance from the second edge to the first corner is less than 10 nm.

3. The nanopore of claim 2 wherein the minimum distance from the second edge to the first corner is less than 2 nm.

4. The nanopore of claim 3 wherein the minimum distance from the second edge to the first corner is less than 1 nm.

5. The nanopore of claim 1 wherein the adjustable mechanism is selected from the group consisting of mechanical positioners, piezoelectric positioners, electromagnetic positioners, and electrostatic positioners.

6. The nanopore of claim 1 further including a mechanism for monitoring the size of the pore.

7. The nanopore of claim 6 wherein the mechanism for monitoring the size of the pore includes the ability to monitor an ionic current through the pore.

8. The nanopore of claim 6 wherein the adjustable mechanism is coupled to the mechanism for monitoring the size of the pore to create a feedback loop for controlling the size of the pore.

9. The nanopore of claim 8 wherein the feedback loop is selected from the group consisting of electronic feedback loops and computer controlled feedback loops.

10. The nanopore of claim 1 wherein at least one of the first and second substrates is a monocrystalline substrate.

11. The nanopore of claim 10 wherein the monocrystalline substrate is selected from the group consisting of silicon, germanium, quartz, and diamond.

12. The nanopore of claim 11 wherein the monocrystalline substrate is selected from the group consisting of silicon, germanium, and diamond, and wherein the monocrystalline substrate has at least one of major surface being substantially perpendicular to a crystalline direction selected from the group consisting of [100] directions, [110] directions, and [111] directions.

13. The nanopore of claim 1 wherein at least one of the first and second substrates is a polycrystalline substrate.

14. The nanopore of claim 13 wherein the polycrystalline substrate is selected from the group consisting of silicon, germanium, quartz, and diamond.

15. The nanopore of claim 1 wherein at least one of the first and second substrates is an amorphous substrate.

16. The nanopore of claim 15 wherein the amorphous substrate is selected from the group consisting of glasses and ceramics.

17. The nanopore of claim 1 wherein the first and second substrates are oriented such that the first corner is opposed by the second edge to form a triangular aperture.

18. The nanopore of claim 17 wherein the triangular aperture is an isosceles triangle.

19. The nanopore of claim 17 wherein the triangular aperture is an asymmetrical triangle.

20. The nanopore of claim 17 further including an angular orientation mechanism to change the relative angle of the second edge to the first corner so as to vary the angles of the triangular aperture.

21. The nanopore of claim 1 wherein the second substrate has a second sharp corner therein, the second corner being bounded by the second surface of the second substrate, the second corner being placed at a termination of the second edge, the second corner having a radius of curvature less than 100 nm, and wherein the first and second substrates are oriented such that the first corner and the second corner combine to form a rhomboidal aperture.

22. The nanopore of claim 21 further including an angular orientation mechanism to change the relative angle of the second corner to the first corner so as to vary the angles of the rhomboidal aperture.

23. The nanopore of claim 1 further including an anti-stiction layer disposed on at least one of the first surface and the second surface.

24. The nanopore of claim 23 wherein the anti-stiction layer is selected from the group consisting of diamond, diamond-like carbon, silicon carbide, a self-assembled monolayer comprising dichlorodimethylsilane, octadecyltrichlosilane, dodecyltrichlorosilane, or perfluorodecyltrichlorosilane, alkanethiols, and molecular films based on the free radical reaction of a primary alkene with hydrogen terminated silicon.

25. A method for fabricating a nanopore, comprising:

providing a first substrate having a flat first major surface, forming a sharp concave first corner in the first substrate, the first corner intersecting the first major surface, providing a second substrate having a flat major second surface, forming a sharp second edge bounded by the second surface, placing the first surface in contact with the second surface in such a fashion that the second edge and the first corner form an aperture, and providing adjustment means to control the minimum distance from the second edge to the first corner.

26. The method of claim 25 wherein the minimum distance between the second edge and the first corner includes a range from zero to 100 nm.

27. The method of claim 25 wherein the first corner is formed utilizing chemical etching.

28. The method of claim 27 wherein the chemical etching comprises orientation-dependent etching.

29. The method of claim 28 wherein the orientation-dependent etching utilizes an etch composition selected from the group consisting of tetramethyl ammonium hydroxide in water, ammonium hydroxide in water, sodium hydroxide in water, a mixture of ethylenediamine and pyrocatechol in water, potassium hydroxide in water, a mixture of potassium hydroxide and isopropanol in water, a mixture of potassium hydroxide and aluminum in water, cesium hydroxide in water, hydrazine in water, and rubidium hydroxide in water.

30. The method of claim 25 wherein the first corner is formed by a procedure selected from the group consisting of cleaving, chipping, spalling, flaking, exfoliating, and knapping.

31. The method of claim 25 wherein the second edge is formed utilizing chemical etching.

32. The method of claim 31 wherein the chemical etching is orientation-dependent etching.

33. The method of claim 32 wherein the orientation-dependent etching utilizes an etch composition selected from the group consisting of tetramethyl ammonium hydroxide in water, ammonium hydroxide in water, sodium hydroxide in water, a mixture of ethylenediamine and pyrocatechol in water, potassium hydroxide in water, a mixture of potassium hydroxide and isopropanol in water, a mixture of potassium hydroxide and aluminum in water, cesium hydroxide in water, hydrazine in water, and rubidium hydroxide in water.

34. The method of claim 25 wherein the second edge is formed by a procedure selected from the group consisting of cleaving, chipping, spalling, flaking, exfoliating, and knapping.

35. The method of claim 25 wherein at least one of the first corner and the second edge is sharpened by oxidative sharpening.

36. The method of claim 25 wherein at least one of the first and second substrates is a monocrystalline substrate.

37. The method of claim 36 wherein the monocrystalline substrate is selected from the group consisting of silicon, germanium, quartz, and diamond.

38. The method of claim 37 wherein the monocrystalline substrate is selected from the group consisting of silicon, germanium, and diamond, and wherein the substrate has at least one of major surface being substantially perpendicular to a crystalline direction selected from the group consisting of [100] directions, [110] directions, and [111] directions.

39. The method of claim 25 wherein at least one of the first corner and the second edge is formed by chemical etching of a hole completely through at least one of the first substrate and the second substrate, respectively.

40. The method of claim 25 further comprising providing an anti-stiction layer on at least one of the first and second surfaces.

41. The method of claim 40 wherein the anti-stiction layer is selected from the group consisting of diamond, diamond-like carbon, silicon carbide, a self-assembled monolayer comprising dichlorodimethylsilane, octadecyltrichlosilane, dodecyltrichlorosilane, or perfluorodecyltrichlorosilane, alkanethiols, and molecular films based on the free radical reaction of a primary alkene with hydrogen-terminated silicon.

42. The method of claim 25 wherein the first and second substrates are oriented such that the first corner is opposed by the second edge to form a triangular aperture.

43. The method of claim 42 wherein said triangular aperture is an isosceles triangle.

44. The method of claim 42 wherein said triangular aperture is an asymmetrical triangle.

45. The method of claim 42 further including providing an angular orientation mechanism to change the relative angle of the second edge to the first corner so as to vary the angles within the triangular aperture.

46. The method of claim 25 wherein the second substrate has a second sharp corner therein, the second corner being bounded by the second surface of the second substrate, the second corner being placed at a termination of the sharp second edge, the second corner having a radius of curvature less than 100 nm, and wherein the first and second substrates are oriented such that the first corner and the second corner combine to form a rhomboidal aperture.

47. The method of claim 46 further including providing an angular orientation mechanism to change the relative angle of the second edge to the first corner so as to vary the angles within the rhomboidal aperture.

48. A method of at least one of characterizing and handling at least one substance selected from the group consisting of molecules, molecular complexes, and supramolecular complexes, comprising:

providing a nanopore having a width, the nanopore including a mechanism for adjusting the width of the nanopore;

placing the nanopore in an ionic solution containing at least one copy of the substance to be characterized so that a continuous path of the ionic solution through the nanopore is established;

adjusting the width of the nanopore to a desired first width;

establishing an ionic electric current of desired direction and magnitude through the nanopore; and sensing at least one of the entrance into the nanopore of the substance to be characterized and the blockage by the nanopore of the path of the substance to be characterized, the sensing occurring by means of a change in the magnitude of the ionic current.

49. The method of claim 48 wherein the substance has a long chain structure.

50. The method of claim 48 wherein variations in ionic current as the substance passes through the adjustable nanopore provide information about the structure of the substance.

51. The method of claim 48 wherein the first width of the adjustable nanopore is small enough to block the passage of the substance at a first point of the structure of the substance.

52. The method of claim 51 wherein, after the passage of the substance is blocked, the width of the nanopore is subsequently increased to a second width sufficient to allow the substance to begin to proceed again through the nanopore.

53. The method of claim 52 wherein monitoring the increasing width of the nanopore to a second width just sufficient to allow the substance to begin to proceed through the nanopore provides information about the structure of the substance.

54. The method of claim 52 wherein the substance has a long chain structure, and wherein after the substance begins to proceed again through the nanopore, the width of the nanopore is subsequently decreased to a third width while the substance is still proceeding through the nanopore.

55. The method of claim 54 wherein the width of the nanopore is decreased to a third width sufficiently small to subsequently block the passage of the substance at a second point along the structure of the substance.

56. The method of claim 55 wherein the third width is less than or equal to the second width, so that the substance becomes trapped by the nanopore between the first point and the second point of the substance.

57. The method of claim 56 wherein at least one of the direction and magnitude of the ionic current is subsequently varied in order to provide information about the structure of the substance.

58. A method of cleaving at least one substance selected from the group consisting of molecules, molecular complexes, and supramolecular complexes, comprising:
providing a nanopore comprising
a first substrate having a sharp concave first corner therein, the first corner being bounded by a first surface of the first substrate, the first corner having a radius of curvature less than 100 nm,
a second substrate having a sharp second edge bounded by a second surface of the second substrate,
wherein the first surface is placed in contact with the second surface so as to create a pore bounded by the first corner and the second edge, and
an adjustable mechanism for increasing and decreasing the width of the nanopore, the width being the minimum distance between the second edge and the first corner;
placing the nanopore in an ionic solution containing at least one copy of the substance to be cleaved so that a continuous path of the ionic solution through the nanopore is established;
adjusting the width of the nanopore to a desired first width;
establishing an ionic electric current of desired direction and magnitude through the nanopore;
sensing the presence in the nanopore of the substance to be cleaved, the sensing occurring by means of a change in the magnitude of the ionic current; and
decreasing the width of the nanopore to a second width small enough to cleave the substance.

59. The method of claim 58, wherein the substance to be cleaved has a long chain structure, and further including employing the nanopore to block the passage of the substance at a desired location along the substance before the substance is cleaved.

60. The method of claim 59, further including employing the nanopore to trap a section of the substance before the substance is cleaved.

61. A method of capturing at least one substance selected from the group consisting of molecules, molecular complexes, and supramolecular complexes, comprising:
providing a nanopore comprising
a first substrate having a sharp concave first corner therein, the first corner being bounded by a first surface of the first substrate, the first corner having a radius of curvature less than 100 nm,
a second substrate having a sharp second edge bounded by a second surface of the second substrate,
wherein the first surface is placed in contact with the second surface so as to create a pore bounded by the first corner and the second edge, and
an adjustable mechanism for increasing and decreasing the width of the nanopore, the width being the minimum distance between the second edge and the first corner;
placing the nanopore in an ionic solution containing at least one copy of the substance to be captured so that a continuous path of the ionic solution through the nanopore is established;
adjusting the width of the nanopore to a desired first width;
establishing an ionic electric current of desired direction and magnitude through the nanopore;
sensing the presence in the nanopore of the substance to be captured, the sensing occurring by means of a change in the magnitude of the ionic current; and
decreasing the width of the nanopore to a second width small enough to capture the substance and hold it.

62. The method of claim 61, wherein the substance to be captured has a long chain structure, and further including employing the nanopore to block the passage of the substance at a desired location along the substance before the substance is captured.

63. The method of claim 62, further including employing the nanopore to trap a section of the substance before the substance is captured.

* * * * *